United States Patent
Nariyuki et al.

(10) Patent No.: US 12,128,339 B2
(45) Date of Patent: Oct. 29, 2024

(54) FILTERING MATERIAL FOR AIR FILTERS AND METHOD FOR MANUFACTURING FILTERING MATERIAL FOR AIR FILTERS

(71) Applicant: Nikki-Universal Co., Ltd., Tokyo (JP)

(72) Inventors: Akane Nariyuki, Tokyo (JP); Mitsuhiro Ishida, Tokyo (JP); Toshiya Nashida, Hiratsuka (JP); Kaori Tozuka, Hiratsuka (JP); Kanako Ina, Hiratsuka (JP)

(73) Assignee: NIKKI-UNIVERSAL CO., LTD., Tokyo (JP)

( * ) Notice: Subject to any disclaimer, the term of this patent is extended or adjusted under 35 U.S.C. 154(b) by 172 days.

(21) Appl. No.: 17/295,716

(22) PCT Filed: Aug. 2, 2019

(86) PCT No.: PCT/JP2019/030473
§ 371 (c)(1),
(2) Date: May 20, 2021

(87) PCT Pub. No.: WO2020/105227
PCT Pub. Date: May 28, 2020

(65) Prior Publication Data
US 2021/0387121 A1    Dec. 16, 2021

(30) Foreign Application Priority Data

Nov. 22, 2018  (JP) ................ 2018-219208
Nov. 22, 2018  (JP) ................ 2018-219210

(51) Int. Cl.
*B01D 39/00*   (2006.01)
*A01N 47/12*   (2006.01)
(Continued)

(52) U.S. Cl.
CPC ......... *B01D 39/1623* (2013.01); *A01N 47/12* (2013.01); *A01N 63/50* (2020.01);
(Continued)

(58) Field of Classification Search
CPC ........ B01D 39/1623; B01D 2239/0442; B01D 2239/0618; A01N 63/50; A01N 47/12
(Continued)

(56) References Cited

U.S. PATENT DOCUMENTS 5,888,526 A * 3/1999 Tsubai ............... D06M 13/355
424/641
2005/0201911 A1   9/2005 Namiki et al.
(Continued)

FOREIGN PATENT DOCUMENTS

CN  1620331 A   5/2005
CN  1767881 A   5/2006
(Continued)

OTHER PUBLICATIONS

International Search Report corresponding to Application No. PCT/JP2019/030473; Date of Mailing: Oct. 29, 2019.
(Continued)

*Primary Examiner* — T. Bennett McKenzie
(74) *Attorney, Agent, or Firm* — CANTOR COLBURN LLP

(57) ABSTRACT

A filtering material for air filters, the filtering material including a base material; and an enzyme-containing antibacterial material, an inorganic anti-allergenic material, and a fungal inhibitor, all being supported on the base material.

4 Claims, 1 Drawing Sheet

(51) Int. Cl.
*A01N 63/50* (2020.01)
*B01D 39/16* (2006.01)

(52) U.S. Cl.
CPC ............... *B01D 2239/0442* (2013.01); *B01D 2239/0618* (2013.01)

(58) Field of Classification Search
USPC ........................................................ 95/285
See application file for complete search history.

(56) References Cited

U.S. PATENT DOCUMENTS

| | | | |
|---|---|---|---|
| 2010/0209530 | A1 | 8/2010 | Yamada |
| 2016/0296871 | A1* | 10/2016 | Scope ................ B01D 46/0028 |
| 2018/0237967 | A1* | 8/2018 | Hossain ............ B01D 39/1623 |

FOREIGN PATENT DOCUMENTS

| | | | | | |
|---|---|---|---|---|---|
| CN | 101175405 | A | | 5/2008 | |
| CN | 101757851 | A | | 6/2010 | |
| CN | 104203366 | A | | 12/2014 | |
| CN | 108554019 | A | | 9/2018 | |
| DE | 102004001590 | A1 | | 8/2005 | |
| JP | H03220376 | A | | 9/1991 | |
| JP | 2000117025 | A | | 4/2000 | |
| JP | 2001029730 | A | | 2/2001 | |
| JP | 2005007345 | A | | 1/2005 | |
| JP | 2005007346 | A | * | 1/2005 | ......... B01D 46/0001 |
| JP | 2005211810 | A | | 8/2005 | |
| JP | 2007050061 | A | | 3/2007 | |
| JP | 2010235701 | A | | 10/2010 | |
| JP | 2011206683 | A | | 10/2011 | |
| WO | 9804334 | A1 | | 2/1998 | |
| WO | 2011062259 | A1 | | 5/2011 | |
| WO | 2012050156 | A1 | | 4/2012 | |
| WO | WO-2013133195 | A1 | * | 9/2013 | ............. A61L 9/014 |

OTHER PUBLICATIONS

PCT International Preliminary Report on Patentability with Written Opinion of the International Searching Authority for 1 corresponding International Application No. PCT/JP2019/030473; Date of Mailing, Jun. 3, 2021.

EPO Extended European Search Report corresponding to Application No. 19887017.2; Mailing date of Jul. 29, 2022.

* cited by examiner

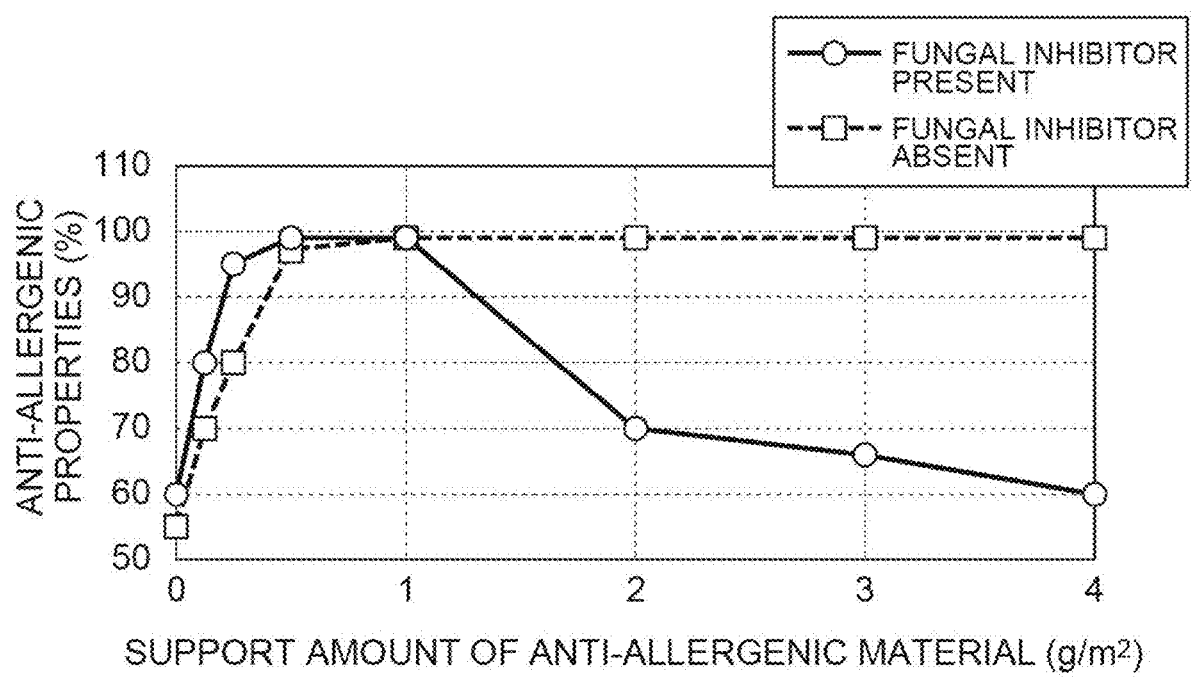

FILTERING MATERIAL FOR AIR FILTERS AND METHOD FOR MANUFACTURING FILTERING MATERIAL FOR AIR FILTERS

CROSS REFERENCE TO RELATED APPLICATIONS

This is the U.S. national stage of application No. PCT/JP2019/030473, filed on Aug. 2, 2019. Priority under 35 U.S.C. § 119(a) and 35 U.S.C. § 365(b) is claimed from Japanese Application No. 2018-219208, filed Nov. 22, 2018, and Japanese Application No. 2018-219210, filed Nov. 22, 2018, the disclosure of which is also incorporated herein by reference.

TECHNICAL FIELD

The present invention relates to a filtering material for air filters and a method for manufacturing a filtering material for air filters.

BACKGROUND ART

In air, harmful substances such as mites, pollens, and bacteria are suspended. Filtering materials for air filters are installed in air purifiers and ventilation apparatuses so as to capture and inactivate these suspended harmful substances (for example, Patent Literatures 1 and 2).

CITATION LIST

Patent Literature

Patent Literature 1: Japanese Unexamined Patent Publication No. 2005-7345
Patent Literature 2: Japanese Unexamined Patent Publication No. 2011-206683

SUMMARY OF INVENTION

Technical Problem

However, it has been found that when a filtering material for air filters manufactured according to conventional technologies is used, there is a risk that the antibacterial properties may be lowered in some cases.

The present invention was achieved in view of such circumstances, and it is an object of the invention to provide a filtering material for air filters, which can exhibit excellent antibacterial properties. It is another object of the present invention to provide a method for manufacturing a filtering material for air filters.

Solution to Problem

The present invention provides a filtering material for air filters, the filtering material comprising a base material; and an enzyme-containing antibacterial material, an inorganic anti-allergenic material, and a fungal inhibitor, all being supported on the base material. The present invention may further comprise a colorant supported on the base material.

Furthermore, the present invention provides a method for manufacturing a filtering material for air filters, the method comprising a first supporting step of supporting a colorant on a base material; and a second supporting step of supporting an enzyme-containing antibacterial material, an inorganic anti-allergenic material, and a fungal inhibitor, on the base material having the colorant supported thereon.

In the present invention, it is preferable that the inorganic anti-allergenic material includes at least one selected from the group consisting of an inorganic solid acid and an inorganic metal salt.

In the present invention, it is preferable that the colorant includes an organic pigment.

In the present invention, it is preferable that the enzyme includes lysozyme.

In the present invention, it is preferable that the support amount of the anti-allergenic material is less than 3 g/m$^2$.

In the present invention, it is preferable that the support amount of the anti-allergenic material is 0.05 g/m$^2$ or more.

In the present invention, it is preferable that the ratio of the support amount of the anti-allergenic material with respect to the support amount of the fungal inhibitor (support amount of anti-allergenic material/support amount of fungal inhibitor) is less than 100.

In the present invention, it is preferable that the fungal inhibitor includes at least one selected from the group consisting of iodopropynyl butylcarbamate, polyaminopropyl biguanide, 2-methyl-4-isothiazolin-3-one, and sodium dehydro acetate.

Advantageous Effects of Invention

According to the present invention, a filtering material for air filters, which can exhibit excellent antibacterial properties (even in a high-temperature, high-humidity environment), can be provided. Furthermore, according to the present invention, a method for manufacturing a filtering material for air filters can be provided.

BRIEF DESCRIPTION OF DRAWINGS

FIG. 1 is a graph showing the relationship between the support amount of an anti-allergenic material and the anti-allergenic properties.

DESCRIPTION OF EMBODIMENTS

[Filtering Material for Air Filters]

A filtering material for air filters of the present embodiment comprises a base material; and an enzyme-containing antibacterial material, an inorganic anti-allergenic material, and a fungal inhibitor, which are supported on the base material.

In the present embodiment, what should be used together with the enzyme-containing antibacterial material is an inorganic anti-allergenic material. According to the findings of the inventors of the present invention, it was found that when an enzyme-containing antibacterial material and an organic anti-allergenic material are used in combination, the antibacterial properties are significantly deteriorated depending on cases. The reason for this is not clearly understood; however, it is speculated that it is probably because the enzyme and the organic anti-allergenic material react or interact with each other, and the enzyme is degraded (deactivated) by the organic anti-allergenic material.

(Base Material)

The material of the base material may be organic fibers or inorganic fibers. Examples of the organic fibers include fibers of cellulose, polypropylene, polyethylene, polyester, polyamide, and the like, and examples of the inorganic fibers include fibers of glass, magnesium silicate, silica, alumina, aluminosilicate, zirconia, and the like. Regarding the morphology of the base material, a nonwoven fabric form, a filter paper form, a honeycomb form, a granular form, a reticulated form, or the like can be adopted, and there are no particular limitations.

The base material may include a flame retardant. Examples of the flame retardant include organic flame retardants, such as bromine compounds such as pentabromodiphenyl ether, octabromodiphenyl ether, decabromodiphenyl ether, tetrabromobisphenol A, and hexabromocyclododecane, chlorine compounds, and phosphoric acid-based compounds such as ammonium phosphate, guanidine phosphate, and melamine phosphate; and inorganic flame retardants such as antimony compounds, and metal hydroxides such as aluminum hydroxide and magnesium hydroxide.

(Antibacterial Material)

Examples of the antibacterial material include inorganic compounds that elute metal ions of silver, copper, zinc, and the like; metal microparticles of silver, copper, zinc, and the like; drugs such as iodine compounds, phenols, quaternary ammonium salts, imidazoles, benzoic acids, hydrogen peroxide, cresol, chlorhexidine, irgasan, aldehydes, and sorbic acid; enzymes; catechins; natural ingredient extracts such as bamboo extracts, Japanese cypress extracts, wasabi (Japanese horseradish) extracts, and mustard extracts. Among these, from the viewpoint of having a bacteriolytic action, an enzyme can be used as an essential component.

Regarding the enzyme, lysozyme, chitinase, protease, glucose oxidase, glucanase, endo-β-N-acetylglucosaminidase, endolysin, and the like may be mentioned as preferred enzymes having a bacteriolytic action. These enzymes may be used singly, or two or more kinds thereof may be used in combination. Furthermore, these enzymes may also be used in combination with other materials such as proteins (excluding enzymes) and peptides having a bactericidal action, or polysaccharides. These other materials may be used singly, or two or more kinds thereof may be used in combination.

Examples of the proteins and peptides include protamine, lactoferrin, and polylysine.

An enzyme, particularly lysozyme, is efficiently glycosylated with a polysaccharide to be chemically covalently bonded to the polysaccharide and exhibits a conspicuous antibacterial action. Examples of the polysaccharide include glucan, dextran, mannan, galactomannan, laminaran, carrageenan, and agarose.

Examples of the combination of an enzyme and a protein or a peptide include lysozyme with protamine, and lysozyme with apolactoferrin. Examples of the combination of an enzyme and a polysaccharide include lysozyme with glucan, and lysozyme with galactomannan.

(Anti-Allergenic Material)

Examples of the inorganic anti-allergenic material include an inorganic solid acid and an inorganic metal salt. Specific examples include inorganic solid acids such as zirconium phosphate, titanium phosphate, and magnesium silicate; and inorganic metal salts such as zinc salts, zirconium salts, aluminum salts, alkaline earth metal salts, and rare earth salts. Among these, zirconium phosphate (lamellar zirconium phosphate) whose crystal system has a lamellar structure is preferred.

Further, by using an antibacterial material and an inorganic anti-allergenic material in combination, deterioration of antibacterial properties particularly in a high-temperature, high-humidity environment can be suppressed. The reason for this is not clearly understood; however, it is speculated to be because as an antibacterial material and an inorganic anti-allergenic material interact with each other, stability is enhanced, and durability is enhanced.

(Fungal Inhibitor)

Examples of the fungal inhibitor include organic iodine compounds, organic nitrogen compounds, organic nitrogen-halogen compounds, organic sulfur compounds, organic acid esters, organic iodine-based imidazole compounds, benzazole compounds, and pyrone-based compounds. More specific examples of the fungal inhibitor include iodopropynyl butylcarbamate, polyaminopropyl biguanide, 2-methyl-4-isothiazolin-3-one, and sodium dehydroacetate.

Further, by using an antibacterial material and a fungal inhibitor in combination, deterioration of antibacterial properties particularly in a high-temperature, high-humidity environment can be suppressed. The reason for this is not clearly understood; however, it is speculated to be because as an antibacterial material and a fungal inhibitor interact with each other, stability is enhanced, and durability is enhanced.

(Other Materials)

The base material may also support a material other than those described above. Examples of such a material include a colorant.

Examples of the material that is used as a colorant include known pigments and dyes. Examples of the pigment include organic pigments such as azo-based, polyazo-based, anthraquinone-based, quinacridone-based, isoindoline-based, isoindolinone-based, phthalocyanine-based, perylene-based, DPP-based pigments, and fluorescent pigments; and inorganic pigments such as carbon black, synthetic silica, chromium oxide, iron oxide, titanium oxide, fired pigments, and zinc sulfide. Examples of the dye include alcohol-soluble dyes, oil-soluble dyes, fluorescent dyes, and light-harvesting dyes. Among these colorants, colorants having a particularly strong deactivating action on lysozyme include organic pigments, oil-soluble dyes, fluorescent dyes, and the like. Among these, suitable colorants may be organic pigments, and specific examples include organic metal complexes such as metal phthalocyanine-based coloring matters, metal naphthalocyanine-based coloring matters, metal porphyrin-based coloring matters, metal azaporphyrin-based coloring matters, bipyridyl metal complexes, terpyridyl metal complexes, phenanthroline metal complexes, bicinchoninic acid metal complexes, azo metal complexes, and quinolinol metal complexes.

(Support Amounts of Various Materials)

It is preferable that the support amount of the antibacterial material is 0.01 to 1 $g/m^2$. Thereby, the antibacterial properties can be maintained satisfactorily. From this point of view, the support amount is more preferably 0.025 to 0.6 $g/m^2$, and even more preferably 0.05 to 0.4 $g/m^2$.

It is preferable that the support amount of the anti-allergenic material is less than 3 $g/m^2$. In a case where an anti-allergenic material and a fungal inhibitor are used in combination, there is a risk that the anti-allergenic properties and antifungal properties may be deteriorated due to an interaction. However, when the support amount is in the above-described range of the support amount, the anti-allergenic properties and antifungal properties can be maintained more satisfactorily. From this point of view, the support amount is more preferably 2 $g/m^2$ or less, even more preferably 1.5 $g/m^2$ or less, and extremely preferably 1 $g/m^2$ or less.

Furthermore, it is preferable that the support amount of the anti-allergenic material is 0.05 $g/m^2$ or more. Thereby, the anti-allergenic properties can be maintained more satisfactorily. From this point of view, the support amount is more preferably 0.075 g/m² or more, and even more preferably 0.1 g/m² or more.

It is preferable that the support amount of the fungal inhibitor is 0.001 to 1 g/m². Thereby, the antifungal properties can be maintained satisfactorily. From this point of view, the support amount is more preferably 0.005 to 0.5 g/m², and even more preferably 0.01 to 0.1 g/m².

It is preferable that the ratio of the support amount of the anti-allergenic material with respect to the support amount of the fungal inhibitor (support amount of anti-allergenic material/support amount of fungal inhibitor) is less than 100. Thereby, the anti-allergenic properties and the antifungal properties can be maintained satisfactorily. Furthermore, in a case where a fungal inhibitor and an anti-allergenic material are used in combination, when the ratio of the support amounts is less than 100, the anti-allergenic properties can be further enhanced as compared to the case of using an anti-allergenic material only. The reason for this is not clearly understood; however, it is speculated to be because the fungal inhibitor activates the anti-allergenic material. From the above-described viewpoint, the ratio of the support amounts is more preferably 75 or less, and even more preferably 50 or less. The lower limit of the ratio of the support amount can be set to more than 0. Further, the support amount of the fungal inhibitor and the support amount of the anti-allergenic material may be appropriately adjusted according to the ratio of the support amounts.

As described above, the inventors found that for the above-described filtering material for air filters, the anti-allergenic properties can be further enhanced by using a fungal inhibitor and an anti-allergenic material in combination, as compared to the case of using an anti-allergenic material only. This is particularly noticeable in a case where the support amount of the anti-allergenic material is small That is, it can be said that a method of enhancing the anti-allergenic properties of a filtering material for air filters comprising a base material; and at least an inorganic anti-allergenic material and a fungal inhibitor supported on the base material, in which the support amount of the anti-allergenic material is adjusted to be less than 3 g/m², and the ratio of the above-described support amounts is adjusted to be less than 100, has been found.

It is preferable that the support amount of the colorant is 0.01 to 10 g/m². Thereby, the base material can be suitably colored. From this point of view, the support amount is more preferably 0.03 to 5 g/m², and even more preferably 0.05 to 1 g/m².

[Method for Manufacturing Filtering Material for Air Filters]

In a case where a colorant is not used, the method for manufacturing a filtering material for air filters can comprise a treatment liquid preparation step of preparing a treatment liquid including an enzyme-contained antibacterial material, an inorganic anti-allergenic material, a fungal inhibitor, other materials as necessary, and a liquid component; a contacting step of bringing the treatment liquid thus prepared into contact with a base material; and a drying step of drying the base material having the treatment liquid attached thereto.

In the treatment liquid preparation step, an enzyme-containing antibacterial material, an inorganic anti-allergenic material, and a fungal inhibitor are mixed with a liquid component. The liquid component may be a water-based component or a non-water-based component such as an alcohol, acetone, or hexane, or the liquid component may also be a component of a mixed system of these. However, from the viewpoint of the dispersibility of the various materials, it is preferable that the liquid component is a water-based component. The amounts of addition of the antibacterial material and the like to the liquid component may be appropriately adjusted such that the support amounts onto the base material become desired amounts.

In the contacting step, the treatment liquid thus obtained is brought into contact with a base material using a dipping method, a spraying method, a gravure printing method, or the like. The selection of which method to use can be appropriately made according to the material and thickness of the base material as an object, wettability of the surface, and the like.

In the drying step, the base material having the treatment liquid attached thereto is dried at 100° C. to 140° C., and the liquid component is removed from the treatment liquid. A multi-cylinder type dryer or the like can be used for drying.

In a case where a colorant is used, the method for manufacturing a filtering material for air filters comprises a first supporting step of supporting a colorant on a base material; and a second supporting step of supporting an enzyme-containing antibacterial material, an inorganic anti-allergenic material, and a fungal inhibitor on the base material having the colorant supported thereon.

In a case where a colorant is used, a colorant and an enzyme-containing antibacterial material are supported on a base material in different supporting steps. According to the findings of the present inventors, it was found that in a case where a colorant and an enzyme-containing antibacterial material are supported by a single supporting step, the antibacterial properties in a high-temperature, high-humidity environment are significantly deteriorated. The reason for this is not clearly understood; however, it is speculated to be because the colorant and the enzyme react with each other at the time of preparing the treatment liquid or at the time of drying the treatment liquid, and the enzyme is degraded (deactivated) by the colorant.

The first supporting step can comprise, more specifically, a first treatment liquid preparation step of preparing a first treatment liquid including a colorant, a binder resin, and a liquid component; a first contacting step of bringing the first treatment liquid thus prepared into contact with a base material; and a first drying step of drying the base material having the first treatment liquid attached thereto. The binder resin is not particularly limited, and examples include an acrylic resin, a urethane resin, a vinyl acetate resin, an SBR resin, an epoxy resin, and a polyvinyl alcohol resin.

The second supporting step can comprise, more specifically, a second treatment liquid preparation step of preparing a second treatment liquid including an enzyme-containing antibacterial material, an inorganic anti-allergenic material, a fungal inhibitor, other materials as necessary, and a liquid component; a second contacting step of bringing the second treatment liquid thus prepared into contact with the base material having the colorant supported thereon through the first supporting step; and a second drying step of drying the base material having the second treatment liquid attached thereto.

In the treatment liquid preparation steps, the object to be supported and a liquid component are mixed. The liquid component may be a water-based component or a non-water-based component such as an alcohol, acetone, or hexane, or the liquid component may also be a component of a mixed system of these. However, from the viewpoint of the dispersibility of the various materials, the liquid component is preferably a water-based component. The amounts of addition of the antibacterial material and the like to the liquid component may be appropriately adjusted such that the support amounts onto the base material become desired amounts.

The contacting steps and the drying steps may be carried out in the same manner as in a case where a colorant is not used.

EXAMPLES

Experiment 1: Antibacterial Properties Test

Example 1

FASTOGEN Green G-58 (manufactured by DIC Corporation) as a colorant (pigment), an acrylic binder, and water were mixed, and a mixed liquid was prepared. A polyester nonwoven fabric having a basis weight of 200 g/m$^2$ and a thickness of 1 mm was impregnated with this mixed liquid, and then the polyester nonwoven fabric was subjected to suction dehydration and was dried in a multi-cylinder type dryer at 120° C. Thereby, a colored polyester nonwoven fabric was obtained.

Next, an enzyme antibacterial agent liquid including 1% by mass of lysozyme as an antibacterial material, a fungal inhibitor liquid including 0.02% by mass of iodopropynyl butylcarbamate as a fungal inhibitor, a zirconium phosphate powder as an inorganic anti-allergenic material, and water were mixed, and a mixed liquid was prepared. The colored polyester nonwoven fabric obtained as described above was impregnated with this mixed liquid, and then the polyester nonwoven fabric was subjected to suction dehydration and was dried in a multi-cylinder type dryer at 120° C. Thereby, a filtering material was obtained.

The support amounts of the various components in the filtering material after drying are shown in Table 1. The support amounts of the various components were 5 g/m$^2$ for the binder, 0.1 g/m$^2$ for the pigment, 0.1 g/m$^2$ for lysozyme, 0.01 g/m$^2$ for iodopropynyl butylcarbamate, and 2 g/m$^2$ for zirconium phosphate.

Comparative Example 1

A filtering material was obtained substantially in the same manner as in Example 1, except that a fungal inhibitor was not used.

Comparative Example 2

A filtering material was obtained substantially in the same manner as in Example 1, except that an inorganic anti-allergenic material was not used.

Comparative Example 3

A filtering material was obtained substantially in the same manner as in Example 1, except that an uncolored polyester nonwoven fabric was used instead of a colored polyester nonwoven fabric, a fungal inhibitor was not used, and polyparavinylphenol (product name: MARUKALINKER M, manufactured by Maruzen Petrochemical Co., Ltd.), which is an organic anti-allergenic material, was used instead of the zirconium phosphate powder as an inorganic anti-allergenic material.

Comparative Example 4

A filtering material was obtained substantially in the same manner as in Example 1, except that polyparavinylphenol, which is an organic anti-allergenic material, was used instead of the zirconium phosphate powder, which is an inorganic anti-allergenic material.

Comparative Example 5

FASTOGEN Green G-58 (manufactured by DIC Corporation), an acrylic binder, an enzyme antibacterial agent liquid including 1% by mass of lysozyme, a fungal inhibitor liquid including 0.02% by mass of iodopropynyl butylcarbamate, a zirconium phosphate powder, and water were mixed, and a mixed liquid was prepared. A polyester nonwoven fabric having a basis weight of 200 g/m$^2$ and a thickness of 1 mm was impregnated with this mixed liquid, and then the polyester nonwoven fabric was subjected to suction dehydration and was dried in a multi-cylinder type dryer at 120° C. Thereby, a filtering material was obtained.

Reference Example 1

A filtering material was obtained substantially in the same manner as in Example 1, except that an uncolored polyester nonwoven fabric was used instead of a colored polyester nonwoven fabric.

The following tests were performed for the filtering materials for air filters obtained in the various examples.

(Antibacterial Properties Test)

A bacterial vapor phase liquid dropping test method was employed as an antibacterial properties test. Specifically, an aqueous solution of *M. luteus* bacterial cells (concentration: 10$^5$ to 10$^7$ CFU/filter) prepared by culturing *M. luteus* bacterial cells in a heart infusion liquid medium, centrifuging, and washing the cells, was prepared. 0.3 mL of this aqueous solution was dropped onto all the require number of sheets of a filtering material to be submitted to evaluation, and then the filtering materials were naturally left to stand in a biosafety cabinet for a predetermined time (untreated filtering material). Subsequently, the bacteria on the filtering material were extracted into a phosphate buffer solution using a vibration mixer. The extracted undiluted solution and a diluted solution were transplanted into a Tryptone soya agar solid medium and cultured at 30° C. for 48 hours, subsequently the number of colonies was measured, and the number of surviving bacteria was calculated. Furthermore, the removal rate of bacterial as an index of antibacterial properties was calculated. The results (untreated) are shown in Table 1.

The above-described untreated filtering material was treated in a predetermined environment, and then the bacterial elimination ratio of the bacteria was calculated in the same manner as described above. The results are shown in Table 1. Meanwhile, in Comparative Examples 3 and 4, since the antibacterial properties were insufficient at the time point of being untreated, an experiment in which the environment was changed was not performed.

TABLE 1

|  |  | Example 1 | Comparative Example 1 | Comparative Example 2 | Comparative Example 3 | Comparative Example 4 | Comparative Example 5 | Reference Example 1 |
|---|---|---|---|---|---|---|---|---|
|  | Supporting step | 2 steps | 2 steps | 2 steps | 1 step | 2 steps | 1 step | 1 step |
| Support | Colorant | 0.1 | 0.1 | 0.1 | — | 0.1 | 0.1 | — |
| amount | Antibacterial material | 0.1 | 0.1 | 0.1 | 0.1 | 0.1 | 0.1 | 0.1 |
| (g/m$^2$) | Fungal inhibitor | 0.01 | — | 0.01 | — | 0.01 | 0.01 | 0.01 |
|  | Inorganic anti-allergenic material | 2 | 2 | — | — | — | 2 | 2 |
|  | Organic anti-allergenic material | — | — | — | 1 | 1 | — | — |
| Antibacterial | Untreated | 99.98≤ | 99.98≤ | 99.98≤ | 87.0 | 86.0 | 99.98≤ | 99.98≤ |
| properties | Room temperature 100% RH humidified 168 hr | 99.98≤ | 99.98≤ | 99.98≤ | — | — | 91 | 99.98≤ |
| (%) | Room temperature 100% RH humidified 504 hr | 99.98≤ | 91.0 | 90.0 | — | — | 85 | 99.98≤ |
|  | 80° C. heating test 168 hr | 99.98≤ | 99.98≤ | 99.98≤ | — | — | 95 | 99.98≤ |
|  | 50° C. 95% RH 168 hr | 99.98≤ | 99.98≤ | 99.98≤ | — | — | 87 | 99.98≤ |
|  | −18° C. low temperature properties test | 99.98≤ | 99.98≤ | 99.98≤ | — | — | 99.98≤ | 99.98≤ |

Experiment 2: Anti-Allergenic Properties Test

Filtering materials for air filters were produced in the same manner as in Example 1, except that the support amount of the inorganic anti-allergenic material was changed as shown in Table 2.

Furthermore, filtering materials for air filters were produced in the same manner as in Comparative Example 1, except that the support amount of the inorganic anti-allergenic material was changed as shown in Table 3.

The following tests were performed for the filtering materials for air filters thus obtained. The respective results are presented in Tables 2 and 3.

(Anti-Allergenic Properties Test)

A piece having an area of 25 cm$^2$ was randomly cut out from a filtering material thus obtained, and this was used as a specimen. This specimen was immersed in a solution of 13 ng/ml of Cryj1 (cedar pollen allergen) as an allergen and then was taken out. After 4 hours passed from the removal, the degree of reduction rate of the allergen (Cryj1) attached to the filtering material was measured by an enzyme-linked immunosorbent assay (ELISA method). An outline of the test method will be described below.

(1) Allergen Measurement Method (ELISA Method)

A primary antibody was immobilized on each well of a 96-well microplate, and the allergen was captured. Next, a secondary antibody that had been labeled in advance was allowed to react, and the enzyme and the substrate were allowed to react in order. The absorbance of each well in which color was developed was measured, and the amount of antigen in the sample was determined from a standard curve.

(2) Reduction Rate Calculation Method

The allergen concentration of an allergen solution that had been reacted with a sample was measured, and the reduction rate obtained by comparing with the concentration of an allergen solution that was not reacted with the sample was determined by the following formula.

Reduction rate(%)=$(B-A)/B \times 100$

A: Allergen concentration in the allergen solution after reaction with the sample
B: Allergen concentration in the allergen solution of the initial solution (Antibacterial Properties Test)
The test was performed in the same manner as in Experiment 1.

(Antifungal Properties Test)
As an antifungal properties test, JIS 2911 (2010) Annex A: Test Method A for Plastic Products was employed. A case where the growth of fungi was not recognized with the naked eye or under a microscope was considered to be acceptable, and a case where the growth of fungi was recognized was considered to be unacceptable.

TABLE 2

| Support amount | | Test results | | |
|---|---|---|---|---|
| Anti-allergenic material (g/m$^2$) | Fungal inhibitor (g/m$^2$) | Anti-allergenic properties (%) | Antibacterial properties (%) | Antifungal properties |
| 0 | 0.01 | 60 | 99.98≤ | Acceptable |
| 0.125 | 0.01 | 80 | 99.98≤ | Acceptable |
| 0.25 | 0.01 | 95 | 99.98≤ | Acceptable |
| 0.5 | 0.01 | 99 | 99.98≤ | Acceptable |
| 1 | 0.01 | 99 | 99.98≤ | Acceptable |
| 2 | 0.01 | 70 | 99.98≤ | Acceptable |
| 3 | 0.01 | 66 | 99.98≤ | Unacceptable |
| 4 | 0.01 | 60 | 95.0 | Unacceptable |
| 5 | 0.01 | 55 | 99.0 | Unacceptable |

TABLE 3

| Support amount | | Test results | |
|---|---|---|---|
| Anti-allergenic material (g/m$^2$) | Fungal inhibitor (g/m$^2$) | Anti-allergenic properties (%) | Antibacterial properties (%) |
| 0 | 0 | 55 | 99.98≤ |
| 0.125 | 0 | 70 | 99.98≤ |
| 0.25 | 0 | 80 | 99.98≤ |
| 0.5 | 0 | 97 | 99.98≤ |
| 1 | 0 | 99 | 99.98≤ |
| 2 | 0 | 99 | 99.98≤ |
| 3 | 0 | 99 | 99.98≤ |
| 4 | 0 | 99 | 99.98≤ |
| 5 | 0 | 99 | 96.0 |

FIG. 1 is a graph showing the relationship between the support amount of an anti-allergenic material and the anti-allergenic properties. That is, FIG. 1 is a graph obtained by plotting the results of Table 2 and Table 3. According to FIG. 1, it is understood that there is a difference in the anti-allergenic behavior depending on the presence or absence of the fungal inhibitor. Particularly, in a region where the support amount of the anti-allergenic material is small, it can be seen that when a fungal inhibitor and an anti-allergenic material are used in combination, the anti-allergenic properties can be further enhanced as compared to a case where only an anti-allergenic material is used.

INDUSTRIAL APPLICABILITY

This invention can be effectively utilized as a filtering material for air filters for capturing and inactivating bacteria, fungi, allergens, and the like suspended in air in hospitals, factories (pharmaceutical and food), cabins, homes, and the like.

The invention claimed is:

1. A filtering material for air filters, the filtering material comprising:
    a base material; and
    an enzyme-containing antibacterial material, an inorganic anti-allergenic material, and a fungal inhibitor, all being supported on the base material,
    wherein the filtering material only includes the inorganic anti-allergenic material and does not include an organic anti-allergenic material,
    the antibacterial material comprises at least one selected from the group consisting of lysozyme, chitinase, protease, glucose oxidase, glucanase, endo-beta-Nacetyl-glucosaminidase, and endolysin,
    the inorganic anti-allergenic material comprises at least one selected from the group consisting of zirconium phosphate, titanium phosphate and magnesium silicate, and
    the fungal inhibitor comprises at least one selected from the group consisting of iodopropynyl butylcarbamate, polyaminopropyl biguanide, 2-methyl-4-isothiazolin-3-one, and sodium dehydroacetate,
    a support amount of the anti-allergenic material is 0.05 $g/m^2$ or more and 0.5 $g/m^2$ or less, and
    a ratio of the support amount of the anti-allergenic material with respect to a support amount of the fungal inhibitor is 12.5 or more and 50 or less.

2. The filtering material for air filters according to claim 1, wherein the inorganic anti-allergenic material includes at least one selected from the group consisting of an inorganic solid acid and an inorganic metal salt.

3. The filtering material for air filters according to claim 1, wherein the enzyme includes lysozyme.

4. The filtering material for air filters according to claim 1, further comprising a colorant supported on the base material.

* * * * *